United States Patent [19]
Inada et al.

[11] Patent Number: 5,916,550
[45] Date of Patent: Jun. 29, 1999

[54] AQUEOUS SUSPENSION OF LOTEPREDNOL ETABONATE

[75] Inventors: Katsuhiro Inada, Kobe; Hideo Terayama, Itami, both of Japan

[73] Assignee: Senju Pharmaceutical Co., Ltd., Osaka, Japan

[21] Appl. No.: 09/035,094

[22] Filed: Mar. 5, 1998

[30] Foreign Application Priority Data

Mar. 14, 1997 [JP] Japan .................................. 9-082207

[51] Int. Cl.⁶ .................................................. A61K 31/74
[52] U.S. Cl. ........................ 424/78.04; 424/434; 424/435
[58] Field of Search ................................ 424/78.04, 434, 424/435

[56] References Cited

U.S. PATENT DOCUMENTS 5,540,930  7/1996  Guy et al. ................................ 424/427

*Primary Examiner*—Carlos A. Azpuru
*Attorney, Agent, or Firm*—Wenderoth, Lind & Ponack, L.L.

[57] ABSTRACT

The conventional aqueous suspension of loteprednol etabonate is not easily amenable to production pH control and entails a pH depression on long-term storage, thus irritating the eye or the nasal mucosa on instillation.

When a C2–7 aliphatic amino acid is added to an aqueous suspension of loteprednol etabonate for topical ophthalmic use, the suspension does not undergo pH depression even on prolonged storage, with the result that no irritable response is elicited in the eye or nasal mucosa.

14 Claims, No Drawings

AQUEOUS SUSPENSION OF LOTEPREDNOL ETABONATE

FIELD OF THE INVENTION

The present invention relates to an aqueous suspension of loteprednol etabonate and more particularly to a stable and safe aqueous suspension of loteprednol etabonate which does not undergo change in pH on prolonged storage and is not irritating to the ocular and nasal mucosa.

BACKGROUND OF THE INVENTION

Many steroid compounds have been used as topical therapeutic agents for eye inflammations. While those steroid compounds show a potent antiinflammatory action, they tend to cause secondary (iatrogenic) disorders of the eye, such as cataract and glaucoma.

Therefore, research has been done to develop steroid compounds which do not cause adverse reactions even when administered topically to the eye and recently loteprednol etabonate (hereinafter sometimes referred to briefly as LE) having very satisfactory antiinflammatory activity and only a low risk for side effects has been developed by modification of prednisolone acetate (U.S. Pat. Nos. 4,716,495 and 4,996,335).

LE is devoid of the 20-keto group in the 17β-position of prednisolone and instead has in this 17β-position an ester residue which is hydrolyzed in vivo to give an inert carboxylic acid metabolite which does not bind to the glucocorticoid receptor. Therefore, unlike many other steroidal agents, LE has a low incidence of side effects such as onset of cataract and elevation of intraocular pressure, thus being a very useful compound for the treatment of ocular inflammations.

Since LE is a substantially water-insoluble crystalline substance, its dosage form has to be an aqueous suspension in order that it may be used as eye drops or nasal drops. However, when LE is formulated with an isotonizing agent such as sodium chloride and a buffer such as phosphoric acid, both of which are conventionally added in the preparation of an aqueous suspension, particles of LE begin to aggregate within 3 months and, in certain cases, within a month.

To overcome this disadvantage, there was proposed an aqueous suspension of LE formulated with a nonionic suspending agent such as polyvinylpyrrolidone (PVP), polyvinyl alcohol (PVA), etc., a nonionic surfactant such as tyloxapol, polysorbate 80, etc., and further an isotonizing agent of polyhydric alcohols such as glycerin and mannitol (PCT/US94-12059) with fairly successful results. However, this formulation makes it difficult to control pH in the preparation of the aqueous suspension and, moreover, when the suspension is stored for a long time, there occurs a pH depression despite little change in appearance so that it elicits an irritable response in the eye or nasal mucosa.

SUMMARY OF THE INVENTION

The inventors of the present invention studied a broad spectrum of compounds for the purpose of improving the above formulation and providing a more stable and safe aqueous suspension which can be easily prepared and even after prolonged storage does not irritate the ocular and nasal mucosa and found surprisingly that certain kinds of amino acids are effective in meeting the above purpose. The finding was followed by further research which has brought the present invention into being.

The present invention, therefore, is directed to:

(1) an aqueous suspension of loteprednol etabonate which comprises loteprednol etabonate and an aliphatic amino acid containing 2–7 carbon atoms, (2) the aqueous suspension (1) wherein said amino acid is one having 1 or 2 amino groups and 1 or 2 carboxyl groups, (3) the aqueous suspension (2) wherein said amino acid is a neutral or acidic amino acid, (4) the aqueous suspension (3) wherein said amino acid is ε-aminocaproic acid, (5) the aqueous suspension (1) which contains 0.01–3 w/v % of loteprednol etabonate and 0.002–2 w/v % of said amino acid in aqueous medium, (6) the aqueous suspension (1) further containing a suspending agent, a nonionic surfactant, and an isotonizing agent, (7) the aqueous suspension (6) which contains 0.2–2 w/v % of the suspending agent, 0.05–1 w/v % of the nonionic surfactant, and 1–6 w/v % of the isotonizing agent in the aqueous medium, (8) the aqueous suspension (6) wherein said suspending agent is a water-soluble nonionic polymer, said nonionic surfactant is a polyoxyalkylene monool or polyol, and said isotonizing agent is a polyhydric alcohol, (9) the aqueous suspension (6) further containing a preservative,

(10) the aqueous suspension (9) which contains 0.0001–0.5 w/v % of said preservative,

(11) the aqueous suspension (6) which contains 0.1–5 moles of said amino acid, 0.01–20 moles of said suspending agent, and 0.05–1 mole of said nonionic surfactant per mole of loteprednol etabonate,

(12) the aqueous suspension (1) wherein loteprednol etabonate occurs in finely divided form with particle diameters within the range of 0.1–30 μm,

(13) the aqueous suspension (1), the pH of which is 4.5–7.0, and

(14) the aqueous suspension (1), (6), or (9) which is an antiinflammatory agent for ophthalmic or otorhinolaryngological use.

DETAILED DESCRIPTION OF THE INVENTION

The particle size of LE suited for preparation of the aqueous suspension of the present invention is generally 0.1–30 μm, preferably 1–20 μm, and more preferably 2–10 μm. It is also preferable that the LE should be produced by a sterile procedure and has a purity of not less than 98 weight %. The concentration of LE in the aqueous suspension need only be therapeutically effective in the treatment of inflammations and is generally 0.01–3 w/v %, preferably 0.05–2 w/v %, and more preferably 0.2–1 w/v %.

The aqueous suspension of the present invention contains an aliphatic amino acid of 2 to 7 carbon atoms, preferably 3–5 carbon atoms, not reckoning the carboxyl group carbon, as a buffer. The number of amino groups in this amino acid is preferably 1 or 2 and more preferably 1. The preferred number of carboxyl groups is 1 or 2. Such amino acid includes neutral amino acids such as alanine, β-aminopropionic acid, γ-aminobutyric acid, ε-aminocaproic acid, etc. and acidic amino acids such as aspartic acid, glutamic acid, etc. Particularly preferred are ε-aminocaproic acid and glutamic acid.

The above amino acid in an aqueous suspension of LE serves to prevent a pH depression of the suspension, and it is likely that this is why the irritation of the ocular and nasal mucosa is alleviated.

The concentration of said amino acid in the aqueous suspension is generally 0.002–2.0 w/v %, preferably 0.01–0.5 w/v %, and more preferably 0.04–0.2 w/v %.

To provide a stable aqueous suspension in accordance with the present invention, a suspending agent, a nonionic surfactant, an isotonizing agent, and, where necessary, a preservative and other additives are incorporated.

The suspending agent need only be a water-soluble polymer and is otherwise not critical in kind. Thus, for example, polyvinylpyrrolidone (PVP), polyvinyl alcohol (PVA), carboxymethylcellulose sodium (CMC. Na), dextrin, cyclodextrin, etc. can be mentioned. Among them, nonionic polymers such as PVP are preferred. The formulating amount of said suspending agent in the aqueous suspension is generally 0.2–2 w/v % and preferably 0.4–1 w/v %.

The nonionic surfactant as well as said suspending agent serves to maintain the active ingredient loteprednol etabonate in evenly suspended state for a long time. The nonionic surfactant that can be used includes polyoxyalkylene monools or polyols which are obtainable by addition-polymerizing 1 or 2 different alkylene oxides, e.g. ethylene oxide and propylene oxide, to an organic compound containing 1 or a plurality of hydroxyl groups per molecule, their esters, and mixtures thereof.

The useful nonionic surfactant includes but is not limited to polysorbate 80, tyloxapol and poloxamers. Among them, tyloxapol and polysorbate 80 are preferred. The formulating amount of the nonionic surfactant is generally 0.05–1 w/v % and preferably 0.1–0.6 w/v %

The isotonizing agent is preferably an aliphatic polyhydric alcohol, particularly an aliphatic polyol containing 2–6 carbon atoms, such as glycerol and mannitol.

The formulating amount of the isotonizing agent in the aqueous suspension is generally 1–6 w/v % and preferably 1.5–4 w/v %. Where necessary, a preservative may be incorporated. The preservative that can be used includes benzalkonium chloride and/or sodium edetate, among others. The formulating amount of the preservative in the aqueous suspension is generally 0.0001–0.5 w/v % and preferably 0.001–0.2 w/v %.

The aqueous suspension of the present invention may further contain therapeutically effective amounts of other drugs such as an antiglaucoma drug, a steroidal or nonsteroidal antiinflammatory agent, an antiallergic agent, an antibacterial agent, and a vasoconstrictor.

The antiglaucoma drug includes but is not limited to betaxolol, atenolol, levobunolol, epinephrine, dipivefrin hydrochloride, pilocarpine hydrochloride, physostigmine salicylate, distigmine bromide, ecothiopate iodide, carteolol hydrochloride, and methazolamide.

The steroidal antiinflammatory agent includes beclomethasone, dexamethasone, betamethasone, fluocinolone, fluorometholone, etc. and the nonsteroidal antiinflammatory agent includes piroxicam, indomethacin, naproxen, phenylbutazone, ibuprofen, and diclofenac sodium, among others.

The antiallergic agent includes but is not limited to sodium cromoglycate, tranilast, ketotifen fumarate, diphenhydramine hydrochloride, etc. and the antibacterial agent includes but is not limited to idoxuridine, erythromycin, sulfisoxazole, tobramycin, and gentamicin. The vasoconstrictor includes naphazoline hydrochloride, among others.

The molar ratio of LE and the above-defined amino acid, suspending agent and nonionic surfactant in the aqueous suspension of the present invention is generally 1:0.1:0.01:0.05 through 1:5:20:1.

The viscosity of the aqueous suspension of the present invention is preferably not over 100 cps. Moreover, the pH of the suspension is preferably within the range of 4.5–7.0 and more preferably within the range of 5.0–6.5.

The aqueous suspension of the present invention can be prepared by the per se known production technology for aqueous suspensions in general. A typical procedure comprises dissolving the suspending agent in water, adding the surfactant, buffer, isotonizing agent, preservative, and other additives sequentially, sterilizing the mixture by filtration or autoclaving, adding pre-sterilized LE, and agitating the whole mixture with a stirrer to provide an aqueous suspension of LE.

The aqueous suspension of LE thus prepared can be used as an ophthalmological or otorhinolaryngological aqueous LE suspension in the prevention and treatment of various inflammations of the eye, ear, nose, or throat.

Taking an ophthalmic aqueous suspension containing 0.5 w/v % of LE according to the present invention as an example, various ocular inflammatory diseases such as allergic conjunctivitis and trachoma can be treated by instilling 0.05–0.1 ml of the suspension in the eye 3 to 10 times daily for one day to one week.

EXAMPLES

The following working and experimental examples are intended to describe the present invention in further detail and should by no means be construed as defining the scope of the invention.

Example 1

Using the routine production procedure for eye drops, eye drops A of the following formulation (Table 1) was prepared.

TABLE 1

| Formula | Eye drops A |
| --- | --- |
| Loteprednol etabonate | 0.5 g |
| Concentrated glycerin | 2.6 g |
| ε-Aminocaproic acid | 0.1 g |
| Tyloxapol | 0.3 g |
| Polyvinylpyrrolidone (K* – 30) | 0.6 g |
| Sodiuin edetate | 0.01 g |
| Benzalkonium chloride (10 w/v %) | 0.05 ml |
| Hydrochloric acid | q.s. |
| Sterilized pure water | to make 100 ml |
| pH | 5.53 |

*K stands for intrinsic viscosity.

Stability Test

Eye drops A according to Example 1 and Eye drops B of the composition available on elimination of ε-aminocaproic acid from the composition used in Example 1 were respectively dispensed into colorless polypropylene bottles and stored at 40° C. and 75% RH for 6 months. Then, the description and pH of each preparation and the mean particle diameter of loteprednol etabonate were evaluated and determined. The results are presented in Table 2. Eye Irritation Study

Method

In this eye irritation test, 0.05–0.1 ml each of Eye drops A and Eye drops B after 6 months of storage at 40° C. and 75% RH were respectively instilled into the eyes of volunteers.

Results

The results of the test are shown in Table 2.

TABLE 2

| | | Eye drops A | Eye drops B |
|---|---|---|---|
| Subject | a | − | − |
| | b | − | + |
| | c | − | + |
| | d | − | + |
| | e | − | + |
| pH | Immediately after preparation | 5.53 | 5.51 |
| | After 6 months of storage (40° C., 75% RH) | 5.11 | 3.85 |
| Mean particle diameter ($\mu$m) | Immediately after preparation | 3.052 | 3.783 |
| | After 6 months of storage (40° C., 75% RH) | Substantially unchanged from the particle diameter recorded immediately after preparation | Substantially unchanged from the particle diameter recorded immediately after preparation |

\#: pain
+: foreign sensation
−: no irritation

It was found that the eye drops containing $\epsilon$-aminocaproic acid does not cause an irritable response in the eye and can be used safely even after 6 month s of storage at 40° C. and 75% RH.

EFFECT OF THE INVENTION

The aqueous suspension of loteprednol etabonate containing a C2–7 aliphatic amino acid according to the present invention has the advantage that it is amenable to production pH control and remains stable without pH depression even on long-term (i.e. 6-month or longer) storage. Therefore, it does not irritate the ocular or nasal mucosa on instillation and hence can be safely administered as eye drops or nasal drops.

We claim:

1. An aqueous suspension of loteprednol etabonate which comprises loteprednol etabonate and an aliphatic amino acid containing 2–7 carbon atoms.

2. The aqueous suspension according to claim 1 wherein said amino acid is one having 1 or 2 amino groups and 1 or 2 carboxyl groups.

3. The aqueous suspension according to claim 2 wherein said amino acid is a neutral or acidic amino acid.

4. The aqueous suspension according to claim 3 wherein said amino acid is $\epsilon$-aminocaproic acid.

5. The aqueous suspension according to claim 1 which contains 0.01–3 w/v % of loteprednol etabonate and 0.002–2 w/v % of said amino acid in aqueous medium.

6. The aqueous suspension according to claim 1 further containing a suspending agent, a nonionic surfactant, and an isotonizing agent.

7. The aqueous suspension according to claim 6 which contains 0.2–2 w/v % of the suspending agent, 0.05–1 w/v % of the nonionic surfactant, and 1–6 w/v % of the isotonizing agent in the aqueous medium.

8. The aqueous suspension according to claim 6 wherein said suspending agent is a water-soluble nonionic polymer, said nonionic surfactant is a polyoxyalkylene monool or polyol, and said isotonizing agent is a polyhydric alcohol.

9. The aqueous suspension according to claim 6 further containing a preservative.

10. The aqueous suspension according to claim 9 which contains 0.0001–0.5 w/v % of said preservative.

11. The aqueous suspension according to claim 6 which contains 0.1–5 moles of said amino acid, 0.01–20 moles of said suspending agent, and 0.05–1 mole of said nonionic surfactant per mole of loteprednol etabonate.

12. The aqueous suspension according to claim 1 wherein loteprednol etabonate occurs in finely divided form with particle diameters within the range of 0.1–30 $\mu$m.

13. The aqueous suspension according to claim 1, the pH of which is 4.5–7.0.

14. A method for treating inflammation of the eye, ear, nose or throat of a patient, which comprises administering an antiinflammatory amount of the aqueous suspension according to claim 1 to the eye, ear, nose or throat of a patient in need thereof.

* * * * *